US006487450B1

(12) United States Patent
Chen (10) Patent No.: US 6,487,450 B1
(45) Date of Patent: Nov. 26, 2002

(54) SYSTEM AND METHOD FOR PREVENTING SUDDEN CARDIAC DEATH BY NERVE SPROUTING FROM RIGHT STELLATE GANGLION

(75) Inventor: Peng-Sheng Chen, La Canada, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 09/513,059

(22) Filed: Feb. 24, 2000

(51) Int. Cl.$^7$ ................................................. A61M 5/00
(52) U.S. Cl. ............................................. 607/9; 607/50
(58) Field of Search .............................. 604/9, 10, 501, 604/119; 128/898

(56) References Cited

U.S. PATENT DOCUMENTS

| | | | | |
|---|---|---|---|---|
| 4,026,300 A | * | 5/1977 | DeLuca et al. | 607/118 |
| 4,573,481 A | * | 3/1986 | Bullara | 607/118 |
| 4,774,967 A | * | 10/1988 | Zanakis et al. | 606/152 |
| 4,919,140 A | * | 4/1990 | Borgens et al. | 607/50 |
| 5,147,294 A | | 9/1992 | Smith et al. | |
| 5,199,428 A | * | 4/1993 | Obel et al. | 600/516 |
| 5,203,326 A | | 4/1993 | Collins | |
| 5,224,477 A | * | 7/1993 | Itoh | 607/152 |
| 5,921,940 A | | 7/1999 | Verrier et al. | |
| 6,351,668 B1 | * | 2/2002 | Chen | 607/2 |
| 6,353,757 B2 | * | 3/2002 | Chen | 128/898 |
| 6,398,800 B2 | * | 6/2002 | Chen | 128/898 |

FOREIGN PATENT DOCUMENTS

| | | |
|---|---|---|
| EP | 0 882 452 A1 | 12/1998 |
| WO | WO 99 39624 A1 | 8/1999 |

OTHER PUBLICATIONS

International Search Report, PCT/US01/0577, issued Sep. 28, 2001.
Schwartz, P.J., et al. "Autonomic Mechanisms in Ventricular Fibrillation Induced by Myocardial Ischemia During Exercise in Dogs with Healed Myocardial Infarction. An Experimental Preparation for Sudden Cardiac Death." PubMed Abstract of *Circulation* Apr; 69(4): 790–800 (1984).

* cited by examiner

*Primary Examiner*—Mark Bockelman
(74) *Attorney, Agent, or Firm*—Sidley Austin Brown & Wood LLP (57) ABSTRACT

A system and method are described for reducing the likelihood of the occurrence of ventricular arrhythmia in the heart of a patient having a myocardial infarction and an atrioventricular block, particularly a ventricular arrhythmia of the type potentially leading to Sudden Cardiac Death. The likelihood of the occurrence of the ventricular arrhythmia is reduced by stimulating myocardial hyperinnervation in the sinus node and right ventricle of the heart of the patient. Myocardial hyperinnervation in the sinus node and right ventricle is stimulated by applying electrical stimulation to the right stellate ganglion of the patient or by applying Nerve Growth Factor or other neurotrophic substance to the right stellate ganglion. The system and method may also be advantageously exploited for use with patients having myocardial infarction but no atrioventricular block and for patients have other heart conditions such as Brugada syndrome.

17 Claims, 4 Drawing Sheets

SYSTEM AND METHOD FOR PREVENTING SUDDEN CARDIAC DEATH BY NERVE SPROUTING FROM RIGHT STELLATE GANGLION

FIELD OF THE INVENTION

The invention generally relates to techniques for preventing heart arrhythmias and in particular to techniques for preventing ventricular arrhythmias of the type that can result in Sudden Cardiac Death.

BACKGROUND OF THE INVENTION

Sudden Cardiac Death ("SCD") claims about 300,000 lives a year in the United States alone. In most cases, the direct cause of SCD is a ventricular tachycardia ("VT") which triggers a ventricular fibrillation ("VF"). VT and VF are different types of ventricular arrhythmias. VT is an abnormally fast ventricular heart rhythm which is, by itself, typically not fatal. VF is a chaotic ventricular heart rhythm which produces little or no net blood flow from the heart, such that there is little or no net blood flow to the brain and other organs. VF, if not terminated, results in death. In most cases of SCD, the victim has a previous myocardial infarction ("MI"), i.e. the patient had a previous heart attack caused by blockage of a portion of the coronary artery which supplies blood to the heart muscle. As a result of the blockage, a portion of the heart muscle does not receive blood and therefore becomes scarred and diseased. The scarred and diseased portion of the heart is referred to as the MI. For several days immediately subsequent to the occurrence of an MI, numerous episodes of VT—referred to as phase one episodes—typically occur. Eventually, the phase one VT episodes largely disappear. Several days or weeks later, though, additional episodes of VT—referred to as phase two episodes—typically begin to occur. It is the phase two episodes of VT that often transition to VF resulting in SCD of the patient. The risk of SCD is even greater if the patient also has an atrioventricular (AV) block, i.e. there is a partial or total interruption of the conduction of electrical impulses from the atria to the ventricles. AV block is common in patients who have had a MI.

Accordingly, it would be highly desirable to develop techniques for preventing VT from occurring, particularly phase two VT in a patients having an MI and, if VT does occur, for preventing the VT from transitioning to a VF. One technique employed in an attempt to prevent VT from occurring is overdrive pacing of the heart. With overdrive pacing, the heart is paced at a rate higher than is intrinsic pacing rate. If VT nevertheless occurs, one or more electrical cardioversion pulses are typically applied to the heart in an attempt to terminate the VT so that the VT does not transition to VF. If VF nevertheless occurs, one or more stronger electrical defibrillation pulses are typically applied to the heart in an attempt to terminate the VF thereby preventing SCD. Hence, for patients that have an MI, particularly a significant one, an implantable cardioverter-defibrillator (ICD) is often implanted into the patient. The ICD includes components for overdrive pacing the heart and for detecting VT or VF and for administering the appropriate therapy. However, the need to frequently overdrive pace the heart and to deliver cardioversion or defibrillation pulses can quickly deplete the battery power of the ICD requiring frequent replacement. Also, the therapies administered by the ICD, particularly the application of cardioversion pulses, may be extremely painful to the patient. Moreover, in some cases, the conventional therapy provided by the ICD is not sufficient to prevent or terminate VF and, accordingly, the patient succumbs to SCD.

Hence, it would also be highly desirable to develop new and more effective techniques for preventing VT or VF from occurring, particularly VT prevention techniques that do not require overdrive pacing and VF prevention techniques that do not require the administration of cardioversion or defibrillation shocks. A reliable prevention technique could greatly reduce need for overdrive pacing or shock therapy, thereby substantially extending the lifetime of the power supply of the ICD and eliminating the need for frequent surgical replacement of the battery supply. Most importantly, techniques for preventing the occurrence of VT or VF reduce the risk of SCD, and hence saves lives. It is to this end that the invention is primarily directed.

SUMMARY OF THE INVENTION

In accordance with one aspect of the invention, a method is provided for reducing the likelihood of the occurrence of an arrhythmia, such as VT or VF, in the heart of a patient. With the method, a neuro-stimulator is implanted in the patient and positioned for applying stimulation to the right stellate ganglion of the patient. Neuro-stimulation is then applied to the right stellate ganglion using the neuro-stimulator so as to stimulate nerve sprouting within portions of the myocardium supplied by nerves from the right stellate ganglion. It is believed that stimulation of nerve growth in the myocardium via the right stellate ganglion results in hyperinnervation of the sinus node and right ventricle of the heart which, in turn, reduces the occurrence of phase-2 VT and VF in the patient, particularly in patients having MI and AV block, and hence reduces the risk of SCD.

In an exemplary embodiment, the neuro-stimulator applies electrical stimulation to the right stellate ganglion. The electrical stimulation is applied at a sub-threshold level wherein the stimulation does not increase the heart rate or blood pressure of the patient. In other embodiments, the neuro-stimulator applies a neurotrophic vector such as Nerve Growth Factor (NGF), neurotrophic chemicals, neurotrophic substances, or neurotrophic hormones to the right stellate ganglion. In still other embodiments, the neuro-stimulator applies gene transfer techniques to cells of the right stellate ganglion to stimulate nerve growth.

In accordance with another aspect of the invention, a method is provided for use with a patient wherein neuro-stimulation is applied to the right stellate ganglion of the patient using a neuro-stimulator so as to stimulate nerve sprouting within portions of the myocardium supplied by nerves from the right stellate ganglion such that the risk of an arrhythmia occurring within the heart of the patient is reduced. Heart signals of the patient are then monitored to detect any arrhythmia that may nevertheless occur within the heart of the patient and, if an arrhythmia is detected, responsive therapy is applied.

In accordance with yet another aspect of the invention, a method is provided wherein a portion of the myocardium is selected wherein hyperinnervation is effective for reducing the occurrence of an arrhythmia in patients and then nerve growth is stimulated along a myocardial nerve pathway supplying nerves to the selected portion of the myocardium. In an exemplary embodiment, the portion of the myocardium selected for hyperinnervation is the sinus node and the right ventricle.

Aspects of the invention are applicable to treating patients with Brugada syndrome as well. Apparatus embodiments of the invention are also provided. Other objects, advantages and features of the invention will be apparent from the detailed descriptions which follow in combination with the attached drawings.

DETAILED DESCRIPTION OF THE EXEMPLARY EMBODIMENTS

Referring to the figures, various techniques for reducing the risk of arrhythmias of the type leading to SCD, particularly within patients having AV block and MI or patients having Brugada syndrome, will now be described. The techniques for reducing the risk of arrhythmias will be described primarily with reference to an implantable system having a neuro-stimulator for inducing hyperinnervation in the sinus node and right ventricle of the heart and an ICD for controlling the neuro-stimulator. However, the techniques for reducing the risk of arrhythmias are also applicable to a wide range of other practical applications not limited for use with ICDs.

Figure 1:
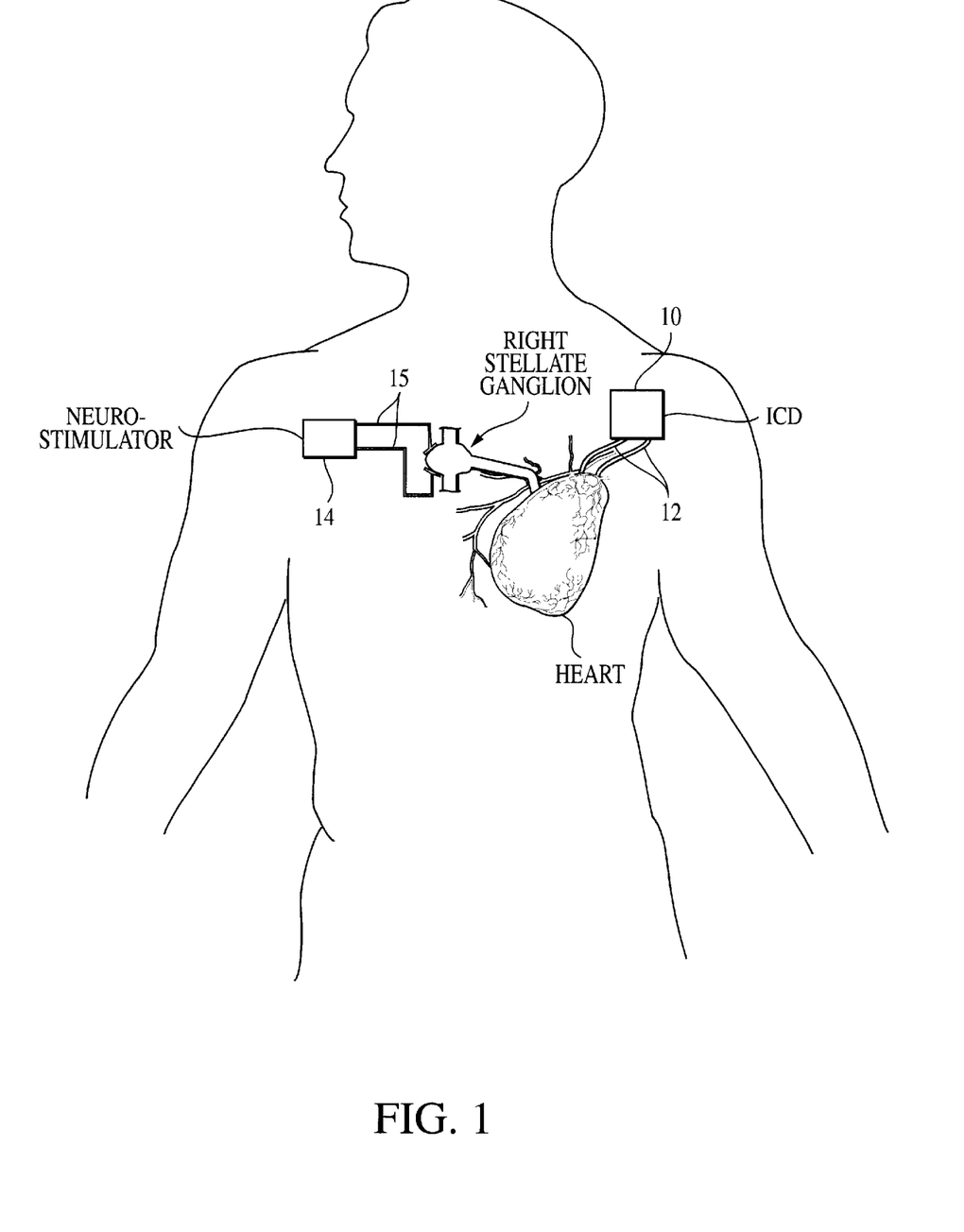
FIG. 1 is a stylized representation of patient having an electrical neuro-stimulator and an ICD implanted therein and particularly illustrating the heart and right stellate ganglion of the patient.

FIG. 1 is a stylized, simplified illustration of a patient, particularly illustrating the heart and the right stellate ganglion of the patient. Although not specifically illustrated in FIG. 1, the heart of the patient may have an AV block and a MI or just an MI. In still other cases, the patient may have Brugada syndrome or other conditions. FIG. 1 also illustrates an ICD 10 having pacing/sensing/defibrillation leads 12 coupled to the heart and a neuro-stimulator 14 having electrical stimulation leads 15 positioned near the right stellate ganglion. Neuro-stimulator 14 is programmed to periodically apply electrical current to the right stellate ganglion to stimulate nerve sprouting within portions of the myocardium supplied by nerves from the right stellate ganglion, particularly the sinus node and right ventricle of the heart. As will be described below, it is believed that such nerve sprouting reduces the risk of ventricular arrhythmias, particularly phase-2 VT which can trigger VF and cause SCD. ICD 10 is programmed to monitor the heart to detect any arrhythmias that may nevertheless arise and to administer appropriate therapy, such as overdrive pacing therapy or cardioversion pulse therapy. The operation of the neuro-stimulator and the ICD may be programmed by one or more external programmers (not shown).

Neuro-stimulator 14 is pre-programmed to apply electrical current to the right stellate ganglion at a level sufficient to stimulate nerve sprouting within the myocardium of the patient via the right stellate ganglion without substantial risk of an increase in either heart rate or blood pressure of the patient. To this end, a threshold current level is pre-determined. The threshold level specifies an electrical stimulation level above which the heart rate or blood pressure may increase as a result of electrical stimulation. The neuro-stimulator is then programmed to a sub-threshold level preferably set to 50% of the threshold level. Depending upon the patient though, other suitable percentages may be employed, such as percentages in the range from 20%–80%. The threshold level may be determined for a particular patient based upon his or her individual response to neuro-stimulation or may be determined based upon values representative of populations of patients. To determine the threshold level based upon the neuro-stimulation response of the particular patient, the method of FIG. 2 may be employed after the neuro-stimulator is implanted into the patient. To determine the threshold level based upon predetermined population information, threshold levels are determined in advance via routine experimentation for a variety of patients of different ages, genders, weights, etc. each having a neuro-stimulator implanted therein. The physician then determines the threshold level for the patient based upon the level previously determined for similar patients. One example of a neuro-stimulator that may be used with the invention is the Medtronic Itrel 7432 neuro-stimulator.

Neuro-stimulator 14 is also pre-programmed to apply the electrical current to the right stellate ganglion periodically, rather than continuously, in an effort to enhance nerve sprouting. The neuro-stimulator may be pre-programmed, for example, to apply stimulation for one second, then apply no stimulation for one second, then apply stimulation again for one second, and so on. Numerous other periodic techniques may be employed to achieve different ratios of stimulation time vs. non-stimulation time. In general, the preferred periodicity of stimulation may be pre-determined by appropriate experimentation based on various patients. For some patients, continuous electrical current may be preferred.

Techniques for reducing ventricular arrhythmias in patients using the system of FIG. 1 will now be described further with reference to FIG. 2. Initially, at step 100, a physician implants the electrical neuro-stimulator into the patient and positions its stimulation leads near the right stellate ganglion. At step 102, the physician implants the ICD into the patient and connects sensing/pacing/defibrillation leads of the ICD to the heart of the patient. At step 104, the physician programs the neuro-stimulator with the pre-determined sub-threshold electrical stimulation level and with the pre-determined stimulation periodicity.

Thereafter, beginning at step 106, the neuro-stimulator periodically applies electrical stimulation at the sub-threshold level to the right stellate ganglion of the patient. It is believed that the application of electrical stimulation to the right stellate ganglion of a results in nerve sprouting within portions of the myocardium, particularly the sinus node and within the right ventricle, which serve to reduce the risk of ventricular arrhythmias of the type that may lead to SCD. Also, beginning at step 108, the ICD continuously monitors heart signals to detect any arrhythmia that may nevertheless occur and to administer responsive therapy. To this end, the ICD analyzes IEGM or other heart signals detected within the heart of the patient to detect VT or VF or other arrhythmias and to administer appropriate therapy. For VT, overdrive pacing may be employed or low level cardioversion shocks may be administered. For VF, higher level defibrillation shocks are preferably administered in an effort to terminate the fibrillation. Thus, in the event an arrhythmia arises within the heart despite the application electrical stimulation to the right stellate ganglion, the ICD administers appropriate therapy. However, as noted, the stimulation of nerve sprouting via the right stellate ganglion may be sufficient to prevent arrhythmias from arising in many patients.

Preferably, also, while the ICD continuously monitors the heart signals to detect an arrhythmia, the ICD also records the heart signals and any responsible therapy, so that the physician may later download the information to determine the number of episodes of arrhythmia, if any, experienced by the patient. Based on this information, the physician may choose to reset the stimulation level or periodicity programmed into the neuro-stimulator, perhaps to increase the stimulation level so as to increase the amount of hyperinnervation of the sinus node and right ventricles. To this end, the physician may review the data recorded by the ICD every three months and adjust the simulation threshold and the periodicity in response to any episodes of ventricular arrhythmia recorded by the ICD or reported by the patient. Steps 106 and 108 are repeated continuously by the ICD and neuro-stimulator as long as deemed necessary by the physician.

Figure 2:
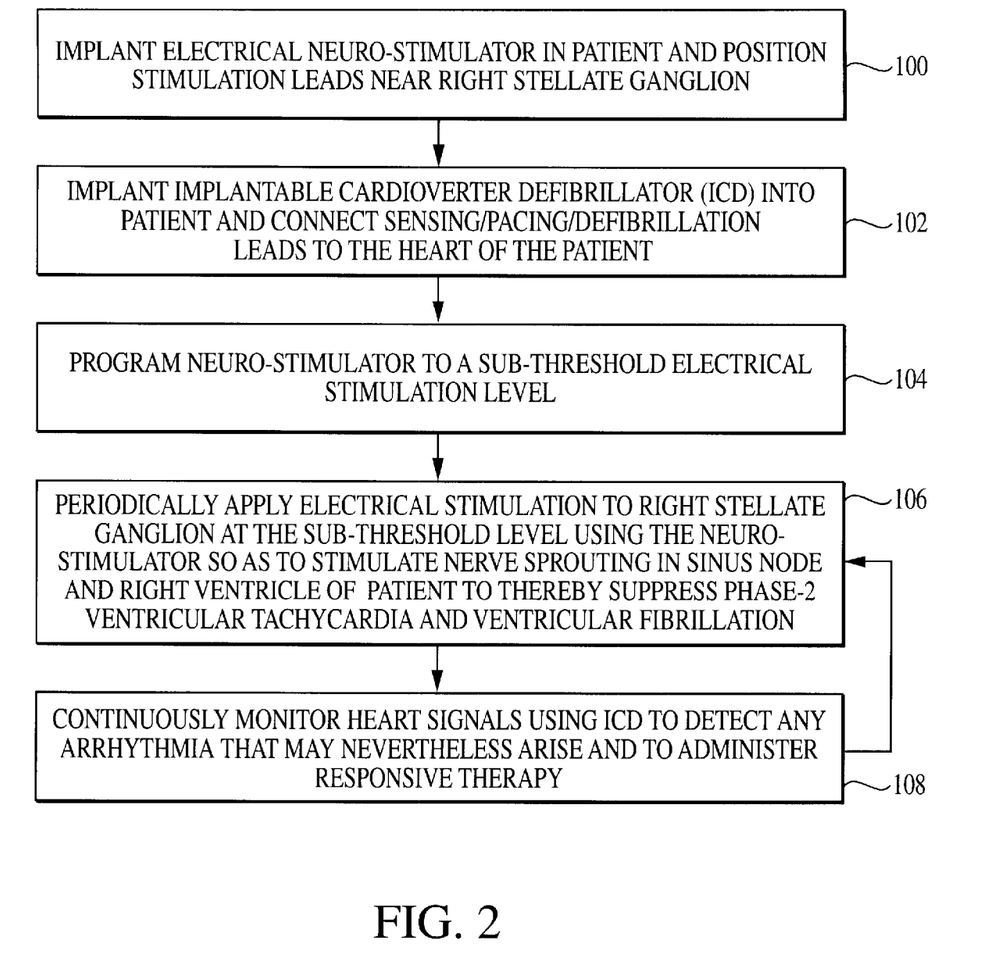
FIG. 2 illustrates a method for reducing the risk of a ventricular arrhythmia in a patient and having the system of FIG. 1 implanted therein.
Figure 3:
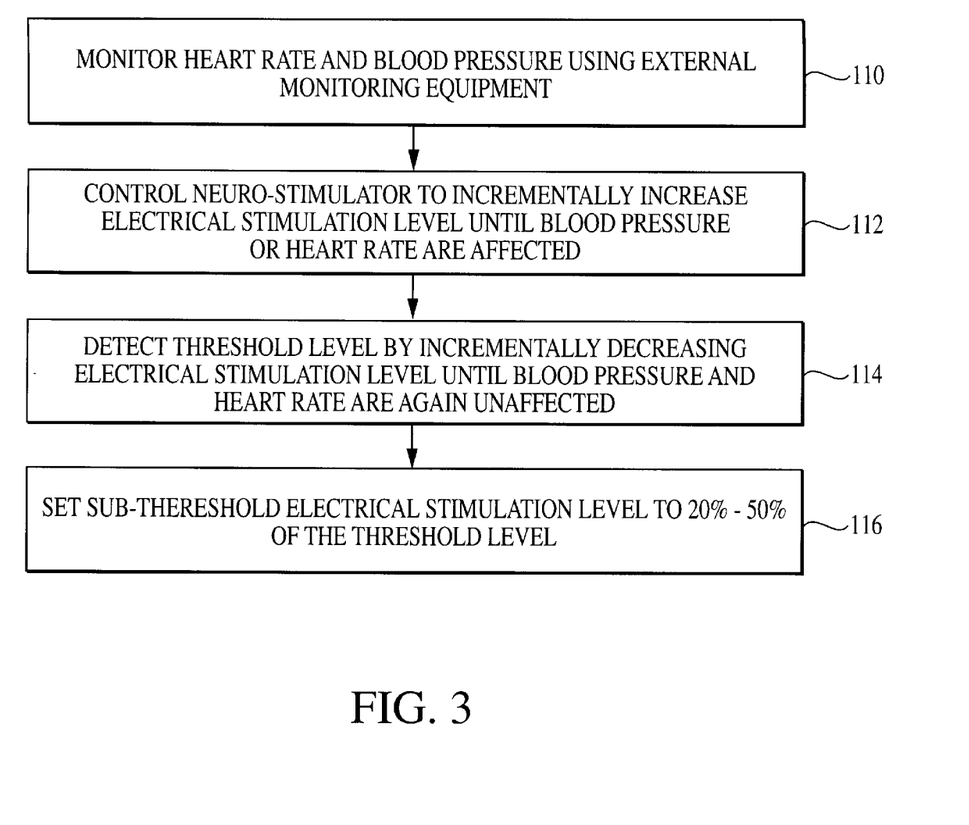
FIG. 3 illustrates a method for determining an electrical stimulation sub-threshold level for use by the neuro-stimulator of FIG. 1.

FIG. 3 illustrates an exemplary method for determining the sub-threshold electrical stimulation level for use in programming the neuro-stimulator within step 104 of FIG. 2. Initially, at step 110, the nominal or base-line heart rate and blood pressure of the patient are determined using external monitoring equipment. This may be performed by a physician using a stethoscope and a sphygmomanometer, or other appropriate heart rate and blood pressure monitoring devices. While monitoring the heart rate and blood pressure, the physician controls the neuro-stimulator, at step 112, to incrementally increase an amount of electrical current applied to the right stellate ganglion from zero current to a level of current sufficient to increase the blood pressure or the heart rate by a pre-determined amount, such as 10%. At step 114, the physician detects the electrical threshold level by then incrementally decreasing the stimulation level of the neuro-stimulator until the blood pressure and heart rate return to the nominal level. Finally, at step 116, the physician sets the sub-threshold electrical stimulation level to 50% of the threshold level to provide a margin for error to help ensure that any stimulation provided by the neuro-stimulator will not affect either the heart rate or blood pressure of the patient. As noted above, at step 104 of FIG. 2, the physician programs the neuro-stimulator to the sub-threshold level.

Thus, FIG. 3 illustrates a manual method for determining the sub-threshold level to be performed by a physician, or other appropriate personnel. Alternatively, the overall system may be configured to permit the sub-threshold level to be automatically determined. In one example, a blood pressure monitoring device is implanted within the patient to automatically detect the blood pressure of the patient. The ICD automatically detects the heart rate of the patient. The neuro-stimulator is configured to receive signals from both the implanted blood pressure monitor and the ICD so that the neuro-stimulator can determine the nominal blood pressure and heart rate. The neuro-stimulator is also configured to perform a threshold detection level search whereby the neuro-stimulator incrementally increases electrical stimulation from zero until the heart rate or blood pressure are increased by the predetermined amount, then the neuro-stimulator incrementally decreases the level of electrical stimulation until the blood pressure and heart rate return to nominal levels. Then, the neuro-stimulator sets the stimulation level to 50% of the detected threshold level. In other implementations, the ICD may be programmed to perform the aforementioned threshold detection level search, with the neuro-stimulator merely receiving stimulation control signals from the ICD. As can be appreciated, numerous implementations may be provided for automatically determining the threshold level.

Figure 4:
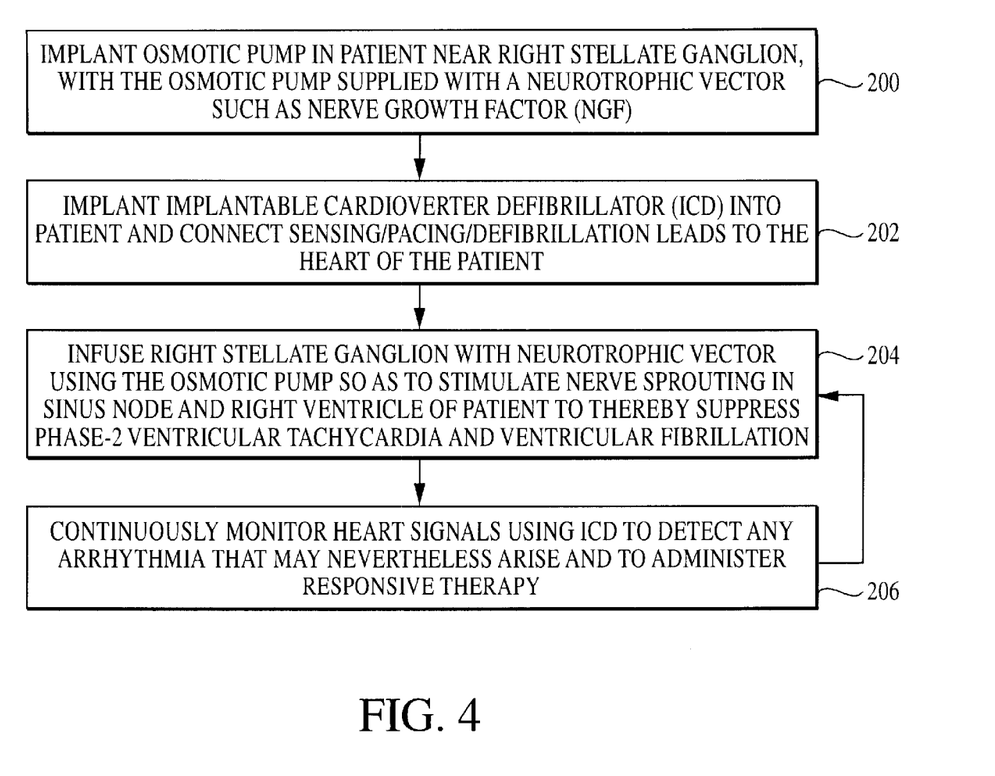
FIG. 4 illustrates an alternative method for reducing the risk of a ventricular arrhythmia in a patient.

What has been described thus far, are techniques for reducing the risk of ventricular arrhythmia within a patient by applying electrical stimulation to the right stellate ganglion. Alternatively, nerve growth may be stimulated using a neurotrophic vector, such as NGF, or by applying gene transfer techniques to cells within the right stellate ganglion. With reference to FIG. 4, a technique for applying a neurotrophic vector to the right stellate ganglion using an osmotic pump will briefly be described. Initially, at step 200, the osmotic pump is implanted in the patient near the right stellate ganglion. The osmotic pump is supplied with a neurotrophic vector such as NGF, a neurotrophic hormone, a neurotrophic chemical, or any other appropriate neurotrophic substance. At step 202, the ICD is implanted within the patient and the sensing/pacing/defibrillation leads are connected to the heart of the patient. Beginning a step 204, the right stellate ganglion is infused with the neurotrophic vector using the osmotic pump so as to stimulate nerve sprouting in portions of the myocardium supplied by nerves from the right stellate ganglion to thereby suppress phase-2 ventricular tachycardia and reduce the risk of ventricular fibrillation. Concurrently, beginning at step 206, the ICD continuously monitors heart signals to detect any arrhythmias that may nevertheless arise and to administer responsive therapy. As with the periodic electrical stimulation method of FIG. 2, the infusion of the neurotrophic vector may be performed periodically or continuously. The optimal periodicity for supplying the neurotrophic vector may be determined using appropriate experimentation techniques based upon populations of patients. For some patients, continuous infusion of the neurotrophic vector may be optimal.

Thus, various techniques have been described for stimulating nerve sprouting in the myocardium via the right stellate ganglion, particularly for use in patients having AV block and MI. Nerve sprouting via the right stellate ganglion in such patients is believed to reduce the risk of ventricular arrhythmias potentially leading to SCD. This belief is based, in part, on studies conducted with adult canine test subjects wherein hyperinnervation of portions of the myocardium using NGF applied to the right stellate ganglion was found to significantly decrease the likelihood of SCD within the test subjects. In each adult canine, an MI and AV block was created and an ICD was implanted. The MI was created by ligating the left anterior descending coronary artery just below the first diagonal branch. The AV block was created by radio-frequency catheter ablation. In a control group of six dogs, no stimulation was applied to the right stellate ganglion. All six dogs showed spontaneous VT after MI, as expected after acute myocardial injury, which persisted for 5.8±2.0 days (phase-1 VT). Spontaneous VT reappeared 13.1±6.0 days after surgery (phase-2 VT). The frequency of phase-2 VT was 0.2±0.2/day. In an experimental group of two other dogs, studied following the studies pertaining to the control group, the right stellate ganglion was continuously infused with NGF via an osmotic pump for over four weeks. The two dogs of the experimental group were followed for 84 and 60 days, respectively. In the initial few days after the MI, the dogs had multiple episodes of phase-1 VT as expected after acute myocardial injury. However, afterwards the dogs did much better than those of the control group. There were no episodes of phase-2 VT during follow up of the two dogs of experimental group. Although, the size of the experimental group may be too small to draw statistical comparisons, the results are certainly encouraging. Moreover, immunohistochemical studies documented the presence of nerve sprouting in the ventricular myocardium. None of the dogs in either group died of SCD.

The results suggest that stimulation of the right stellate ganglion can trigger nerve sprouting in the ventricular myocardium and that nerve sprouting originating from the right stellate ganglion is protective against phase-2 VT. Since phase-2 VT can often trigger VF and ultimately SCD, it is believed that stimulation of the right stellate ganglion is protective against SCD within at least some patients, particularly patients having AV block and an MI. Although the experiments were performed with adult canine subjects using NGF applied to the right stellate ganglion, it is believed that similar results would occur in human patients wherein either NGF or electrical stimulation is applied to the right stellate ganglion.

One possible explanation as to why stimulation of the right stellate ganglion is protective against phase-2 VT within patients having AV block and MI is as follows. The healthy myocardium has natural electrical heterogeneity in which the right ventricular epicardial cells have a much stronger transient outward current than the left ventricular epicardial cells. This heterogeneity does not have significant clinical consequences in normal hearts. However, when the ion channels in the heart are altered by either genetic mutations or by electrical remodeling after MI and AV block, this heterogeneity may be amplified and cause arrhythmia. Sympathetic stimulation via the right stellate ganglion reduces the electrical heterogeneity in these patients and thereby prevents arrhythmia. For example, in Brugada syndrome, infusion of isoproterenol (a form of sympathetic stimulation) during the electrical storm (clustering of VF attacks) may be very efficacious in preventing VF and SCD. By applying stimulation to the right stellate ganglion, nerve sprouting is enhanced within portions of the myocardium consistent with the natural electrical pathways, at least partially counteracting the electrical re-modeling triggered by the MI or by the genetic abnormalities such as Brugada syndrome. Hence, there is less risk that abnormal heart rhythms will arise, particularly phase-2 VT which may trigger VF and cause SCD. However, regardless of the particular mechanism from which the decreased risk of SCD arises, the technique of the invention is believed to be effective for decreasing the likelihood of SCD.

What has been described are various techniques for decreasing the likelihood of ventricular arrhythmias in patients, particularly arrhythmias of the type that may trigger SCD. Aspects of the techniques have been described primarily with reference to the flowchart of FIGS. 2–4. Each block within the flowcharts illustrates both a method step and an apparatus element for performing the method step. Specific method steps may be performed, as described above, using an ICD and neuro-stimulator or other suitable devices. Many of the method steps need not necessarily be performed in the order illustrated.

Also, although described primarily with respect to techniques for preventing SCD within patients having AV block and MI, general techniques of the invention may also be applied to other disease processes. Specifically, this method may be particularly useful for the Brugada syndrome. Brugada syndrome is defined by right bundle branch block and persistent ST segment elevation on the electrocardiogram (ECG) and a high probability of SCD. The ST segment of the ECG is between the end of ventricular depolarization (i.e. the end of the R-wave) and the beginning of ventricular re-polarization (i.e. the beginning of the T-wave). Recently, some investigators reported that sympathetic stimulation by isoproterenol infusion might normalize the ECG and in some patients, and help prevent VF and SCD. However, because isoproterenol should be given only in the hospital, it is used only for treatment of Brugada syndrome when there is a clustering of attacks of VF. It is used chronically to prevent VF or SCD. The invention described herein may be extremely useful in patients with Brugada syndrome by stimulating the sympathetic nerve growth in the right ventricle. The increased sympathetic tone will decrease the frequencies of VF and SCD. Therefore, the invention is not limited to patients with MI and AV block. Indeed, the invention may be advantageously exploited in still other situations where elevated sympathetic tone in the right ventricle helps reduce electrophysiological heterogeneity and thereby reduce ventricular arrhythmia.

In general, the method and apparatus embodiments illustrated with reference to the drawings and described herein are merely illustrative of principles of the invention which may be implemented in alternative embodiments to achieve other ends than those specifically described herein.

I claim:

1. A method for reducing the likelihood of the occurrence of an arrhythmia in the heart of a patient, said method comprising the steps of:

implanting a neuro-stimulator in the patient positioned for applying stimulation to the right stellate ganglion of the patient; and applying neuro-stimulation to the right stellate ganglion using the neuro-stimulator so result in nerve sprouting within portions of the myocardium supplied by nerves from the right stellate ganglion.

2. A method for use with a patient, said method comprising the steps of:

applying neuro-stimulation to the right stellate ganglion of the patient using a neuro-stimulator result in nerve sprouting within portions of the myocardium supplied by nerves from the right stellate ganglion such that the risk of an arrhythmia occurring within the heart of the patient is reduced; and monitoring heart signals of the patient to detect any arrhythmia that may nevertheless occur within the heart of the patient and, if an arrhythmia is detected, applying responsive therapy.

3. A method for reducing the risk of a ventricular arrhythmia in the heart of a patient, said method comprising the steps of:

selecting a portion of the myocardium wherein hyperinnervation is effective for reducing the likelihood of ventricular arrhythmias in patients; and stimulating nerve growth along a myocardial nerve pathway supplying nerves to the selected portion of the myocardium, so that nerve sprouting results, whereby the risk of the ventricular arrhythmia is reduced.

4. The method of claim 3 wherein the patient has a myocardial infarction (MI) and the ventricular arrhythmia is a phase-2 ventricular tachycardia.

5. The method of claim 4 wherein the patient has atrioventricular (AV) block.

6. The method of claim 3 wherein the patient has Brugada syndrome.

7. The method of claim 3 wherein the step of selecting a portion of the myocardium wherein hyperinnervation is effective for reducing the occurrence of the arrhythmia includes the step of selecting one or more of the sinus node or the right ventricle.

8. The method of claim 7 wherein the step of stimulating nerve growth along a myocardial nerve pathway supplying nerves to the selected portion of the myocardium includes the step of applying electrical stimulation signals to the myocardial nerve pathway.

9. The method of claim 8 wherein the electrical stimulation is applied below a threshold level above which the electrical stimulation causes an increase in heart rate or blood pressure.

10. The method of claim 9 further including the step of:
determining nominal levels for the heart rate and blood pressure of the patient; and
determining the threshold level by increasing an amount of electrical stimulation applied to the myocardial nerve pathway until the heart rate or blood pressure of the patient increases above the nominal levels by a predetermined amount, then decreasing the amount of electrical stimulation until the heart rate and blood pressure returns to the nominal levels, with the resulting amount of electrical stimulation being identified as the threshold level.

11. The method of claim 10 wherein the electrical stimulation is applied at a sub-threshold level set based on the threshold level.

12. The method of claim 11 wherein the sub-threshold level is 50% of the threshold level.

13. The method of claim 8 wherein the electrical stimulation is applied using an implanted neuro-stimulator.

14. The method of claim 7 wherein the step of stimulating nerve growth along a myocardial nerve pathway supplying nerves to the selected portion of the myocardium includes the step of applying a neurotrophic vector to a portion of the myocardial nerve pathway.

15. The method of claim 14 wherein the neurotrophic vector is selected from a group including Nerve Growth Factor, neurotrophic chemicals, and neurotrophic hormones.

16. The method of claim 3 wherein the step of stimulating nerve growth along the myocardial nerve pathway supplying nerves to the selected portion of the myocardium includes the step of stimulating nerve growth via the right stellate ganglion of the patient.

17. The method of claim 3 wherein the ventricular arrhythmia is a phase-2 ventricular tachycardia.

* * * * *

UNITED STATES PATENT AND TRADEMARK OFFICE
CERTIFICATE OF CORRECTION

PATENT NO. : 6,487,450 B1
DATED : November 26, 2002
INVENTOR(S) : Peng-Sheng Chen It is certified that error appears in the above-identified patent and that said Letters Patent is hereby corrected as shown below:

Column 4,
Line 14, please insert the word -- heights, -- after the word "genders," and before the word "weights".

Column 8,
Line 26, please insert the phrase -- as to -- after the word "so" and before the word "result".
Line 28, please delete the period after the word "ganglion" and insert therefor -- , whereby the likelihood of the arrhythmia occurring is reduced. --.
Line 32, please insert the phrase -- so as to -- after the word "neuro-stimulator" and before the word "result".

Signed and Sealed this

Twentieth Day of May, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,487,450 B1
APPLICATION NO. : 09/513059
DATED : November 26, 2002
INVENTOR(S) : Peng-Sheng Chen It is certified that error appears in the above-identified patent and that said Letters Patent is hereby corrected as shown below:

Beginning at column 1, line 6, under the title, please insert the following:

--GOVERNMENT LICENSE RIGHTS

The U.S. Government has a paid-up license in this invention and the right in limited circumstances to require the patent owner to license others on reasonable terms as provided for by the terms of Grant Nos. 1P01HL078931, R01HL52319, R01HL71140 and R01HL78932 awarded by the National Institutes of Health.--

Signed and Sealed this

Thirteenth Day of April, 2010

David J. Kappos
*Director of the United States Patent and Trademark Office*